(12) United States Patent
Thomas et al.

(10) Patent No.: US 9,061,113 B2
(45) Date of Patent: Jun. 23, 2015

(54) FOREHEAD SUPPORT FOR A FACIAL MASK

(75) Inventors: Jonathan Huw Thomas, Vale of Glamorgan (GB); Enrico Brambilla, Drummoyne (AU); Renee Frances Doherty, Coogee (AU); Philip John Gunning, North Rocks (AU); Michiel Kooij, Camperdown (AU); Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 813 days.

(21) Appl. No.: 12/213,584

(22) Filed: Jun. 20, 2008

(65) Prior Publication Data
US 2008/0314389 A1 Dec. 25, 2008

(30) Foreign Application Priority Data
Jun. 22, 2007 (AU) ................................. 2007903361

(51) Int. Cl.
*A62B 18/08* (2006.01)
*A61M 16/06* (2006.01)

(52) U.S. Cl.
CPC .............. *A61M 16/06* (2013.01); *A62B 18/084* (2013.01); *A61M 16/0633* (2014.02)

(58) Field of Classification Search
CPC . A61M 16/06; A61M 16/0633; A62B 18/804
USPC .............. 128/206.21, 206.24, 207.11, 206.27
See application file for complete search history.

(56) References Cited

U.S. PATENT DOCUMENTS

| | | | | |
|---|---|---|---|---|
| 4,621,378 A | * | 11/1986 | Hatchman | ............................. 2/9 |
| 4,825,878 A | * | 5/1989 | Kuntz et al. | ................... 128/857 |
| 5,074,297 A | * | 12/1991 | Venegas | ................... 128/204.18 |
| 5,660,174 A | * | 8/1997 | Jacobelli | ................... 128/206.24 |
| 5,991,915 A | * | 11/1999 | Moorhouse | ......................... 2/12 |
| 6,119,693 A | | 9/2000 | Kwok et al. | |
| 6,532,961 B1 | | 3/2003 | Kwok et al. | |
| 6,805,117 B1 | * | 10/2004 | Ho et al. | ................... 128/201.22 |
| 6,823,869 B2 | | 11/2004 | Raje et al. | |

(Continued)

FOREIGN PATENT DOCUMENTS

| | | |
|---|---|---|
| JP | 2006-506109 | 2/2006 |
| JP | 2008-502380 | 1/2008 |

(Continued)

OTHER PUBLICATIONS

Office Action issued in related European Appln. No. 08158803.0 (Jan. 11, 2011).

(Continued)

*Primary Examiner* — Tan-Uyen (Jackie) T Ho
*Assistant Examiner* — Aundria Hairell
(74) *Attorney, Agent, or Firm* — Nixon & Vanderhye P.C.

(57) ABSTRACT

A respiratory mask includes a mask frame, a forehead support provided to the mask frame and including a forehead member, and headgear including at least one strap adapted to connect to the forehead member. The forehead member includes one or more holes configured and positioned to allow at least one strap to form a strap loop that loops around at least a portion of the forehead member and arrange one or more layers of the strap loop between the headgear member and the patient's forehead in use.

45 Claims, 9 Drawing Sheets

(56) References Cited

U.S. PATENT DOCUMENTS

| | | | | |
|---|---|---|---|---|
| 7,036,508 | B2* | 5/2006 | Kwok | 128/207.11 |
| 7,047,971 | B2 | 5/2006 | Ho et al. | |
| 7,069,932 | B2* | 7/2006 | Eaton et al. | 128/206.24 |
| 7,216,647 | B2 | 5/2007 | Lang et al. | |
| 7,296,575 | B1* | 11/2007 | Radney | 128/207.11 |
| 2002/0074001 | A1* | 6/2002 | Kwok et al. | 128/207.13 |
| 2003/0172936 | A1* | 9/2003 | Wilkie et al. | 128/207.18 |
| 2004/0045551 | A1* | 3/2004 | Eaton et al. | 128/206.21 |
| 2004/0182398 | A1* | 9/2004 | Sprinkle et al. | 128/207.13 |
| 2004/0211428 | A1* | 10/2004 | Jones et al. | 128/206.27 |
| 2005/0268916 | A1 | 12/2005 | Mumford et al. | |
| 2006/0053658 | A1* | 3/2006 | Voughlohn | 36/50.1 |
| 2006/0249157 | A1 | 11/2006 | Eaton et al. | |
| 2011/0048425 | A1* | 3/2011 | Chang | 128/206.24 |

FOREIGN PATENT DOCUMENTS

| | | |
|---|---|---|
| WO | WO 03/082406 | 10/2003 |
| WO | WO 03/090827 | 11/2003 |
| WO | WO 2005/002656 | 1/2005 |
| WO | WO 2005/009521 | 2/2005 |
| WO | WO 2005/123166 | 12/2005 |
| WO | WO 2006/074517 | 7/2006 |
| WO | WO 2006/113321 | 10/2006 |

OTHER PUBLICATIONS

Examination Report issued Jun. 20, 2008 in New Zealand Appln. No. 569153.
U.S. Appl. No. 60/858,694, filed Nov. 2006, Chu et al.
Office Action issued in European Appln. No. 08158803.0 (Dec. 4, 2009).
European Search Report, Appln. EP 08158803, Feb. 9, 2009.
Examination Report issued in related New Zealand Appln. No. 591863 (Mar. 30, 2011).
Examination Report issued in a related New Zealand Application No. 591863, dated Jul. 12, 2012.
Office Action issued in a corresponding Japanese Appl. No. 2008-162512 (Oct. 23, 2012) with English translation thereof.
Office Action issued in related Chinese Appln. No. 200810126987.6 (Feb. 3, 2012).
Second Office Action dated Dec. 13, 2012 issued in related CN Application No. 200810126987.6.
Office Action issued in a corresponding Chinese Appln. No. 200810126987.6, dated Jun. 21, 2013 with English translation thereof.
Office Action issued in a corresponding Japanese Appl. No. 2008-162512, dated Jul. 30, 2013, with English translation thereof.

* cited by examiner

Fig. 2-13B ial Patent Application No. AU 2007903361, filed Jun. 22, 2007, which is incorporated herein by reference in its entirety.
FOREHEAD SUPPORT FOR A FACIAL MASK

CROSS-REFERENCE TO APPLICATION

This application claims the benefit of Australian Provisional Patent Application No. AU 2007903361, filed Jun. 22, 2007, which is incorporated herein by reference in its entirety.

FIELD OF THE INVENTION

The present invention relates to respiratory masks, and in particular, forehead supports, forehead pads, and headgear for respiratory masks.

BACKGROUND OF THE INVENTION

A respiratory mask is generally comprised of a frame, sealing cushion, air delivery elbow, adjustable forehead support having one or more forehead pads, and headgear.

The forehead support serves to stabilize the mask on the patient's face and ensures that the cushion locates correctly on the patient's facial profile. The forehead support generally anchors the frame in such a way as to allow the frame and cushion to pivot around the forehead pad so that the cushion does not collapse under headgear tension. This maintains the cushion in sealing abutment with the patient's face.

The purpose of the headgear is to stabilize the mask, including the forehead support and cushion, at the chosen location on the patient's face. This helps to reduce leak around the cushion.

It is generally preferable that areas of mask contact with the patient's face feel soft to the patient and distribute headgear tension forces over an area.

A typical forehead support comprises a generally T-shaped or I-shaped rigid or semi-rigid component having a pair of forehead pads attached thereto, and having one or more hooks, slots or clip receptacles adapted to engage with headgear straps. See U.S. Pat. Nos. 6,119,693, 6,532,961, and 7,216,647, published PCT Application No. WO 2006/074517, and U.S. Provisional Application No. 60/858,694.

Forehead pads are typically cut from foam, molded or extruded in silicone, or constructed from a soft, comfortable material in contrast to the more rigid material of the forehead support, which is often molded from a polycarbonate material.

Other forms of mask may include a semi-rigid stabilizing structure having a fabric and foam layer stitched or otherwise attached thereto. See published PCT Application No. WO 2003/090827.

SUMMARY OF THE INVENTION

A first aspect of the invention is to provide a low cost, comfortable forehead support that is easy to use.

According to a second aspect of the invention, headgear is provided for a respiratory mask, wherein at least a portion of the headgear forms a soft medium between the patient's forehead and the forehead support of the mask.

Advantageously, under headgear tension, the headgear acts as padding between the patient's forehead and the forehead support increasing patient comfort by: (a) distributing the load over a large portion of the forehead to avoid forming high pressure contact regions, (b) providing a soft and/or warm to touch contact surface, and (c) interposing a deformable medium between the forehead support and the patient's forehead to ensure that the largest possible portion of the forehead is contacted by the forehead support, reducing the average pressure.

Another benefit of embodiments of the invention is that specific forehead pads (e.g., as are typically provided on the ResMed Ultra Mirage Mask) become redundant and so the cost of goods, assembly complexity, and/or assembly time are reduced.

According to a third aspect of the invention, headgear is provided for a respiratory mask that is adapted for releasable attachment to a forehead support of the mask.

According to a fourth aspect of the invention, headgear is provided for a respiratory mask, wherein at least a portion of the headgear forms a soft medium between the patient's forehead and the forehead support of the mask, wherein the headgear is made from flexible straps.

In one form, two front headgear straps pass over the patient's forehead and each have a loop formed at an end region. These loops are in adjacent opposing relation in use.

In one form, the headgear includes a forehead member that acts to reinforce at least a portion of the headgear adjacent the patient's forehead. The forehead member may extend laterally along the patient's forehead and may be provided either integrally with the forehead support or as a separate member. The forehead member may be releasably or permanently attached to the headgear.

In one form, each of the front headgear straps loops through an aperture in the forehead member or forehead support. Each strap loop may be located on either or both sides (i.e., side closest to patient's face and side furthest away) of the forehead member or forehead support. One advantage of locating both sides of each strap loop adjacent an inside surface of the forehead member or forehead support is that a double layer of headgear is provided between the patient's forehead and the forehead member or forehead support. This double layer of headgear serves as padding and can increase patient comfort.

In one form, each front headgear strap may bifurcate into two straps being spaced apart and having ends that are looped and secured to either the forehead member or forehead support in a similar manner as above. Advantageously, this provides a more stable abutment of the straps on the patient's forehead.

In one form, each headgear strap or strap loop may pass through the forehead member or forehead support, one, two or more times so that the strap is secured in a stable manner.

The loop may be closed by Velcro attachment, sewing, a buckle or other suitable means. The buckle may be provided in the forehead member of forehead support.

It should be noted that the mask may be any type of facial mask, in particular of the type adapted for respiratory therapies and could take the form of a full face mask, a nasal mask, nasal pillows, or any other type of mask.

Another aspect of the present invention relates to a respiratory mask including a mask frame, a forehead support provided to the mask frame and including a forehead member, and headgear including at least one strap adapted to connect to the forehead member. The forehead member includes one or more holes configured and positioned to allow at least one strap to form a strap loop that loops around at least a portion of the forehead member and arrange one or more layers of the strap loop between the headgear member and the patient's forehead in use.

Another aspect of the present invention relates to a respiratory mask including a mask frame, a forehead support provided to the mask frame and including a forehead member, and headgear including first and second straps. The forehead member includes one or more holes configured and positioned to allow the first and second straps to form first and second strap loops that loop around respective portions of the forehead member, and the strap loops are asymmetrically arranged with respect to a vertical plane of symmetry of the forehead member.

Another aspect of the present invention relates to a respiratory mask including a mask frame, a forehead support provided to the mask frame and including a forehead member with a first width, a flexible beam including a second width that is wider than the first width, and headgear including first and second straps. The forehead member and the flexible beam each include openings configured and positioned to allow the first and second straps to form first and second strap loops that loop around respective portions of the forehead member and the flexible beam, and a layer of each strap loop is arranged between the flexible beam and the patient's forehead to prevent contact of the flexible beam and the patient's forehead in use.

Another aspect of the present invention relates to a respiratory mask including a mask frame, a forehead support provided to the mask frame, and headgear including at least one strap adapted to connect to the forehead support. The at least one strap bifurcates into two, spaced-apart straps that are looped around at least a portion of the forehead support to arrange a layer of each of the spaced-apart straps between the forehead support and the patient's forehead.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 2-1 is a cross-sectional view illustrating a forehead support with symmetrical straps according to an embodiment of the present invention;

FIG. 2-1-1 is a schematic view of a forehead member with locating rims according to an embodiment of the present invention;

FIG. 2-2 is a cross-sectional view illustrating a forehead support with symmetrical straps according to another embodiment of the present invention;

FIG. 2-3 is a cross-sectional view illustrating a forehead support with symmetrical straps according to another embodiment of the present invention;

FIG. 2-4 is a cross-sectional view illustrating a forehead support with symmetrical straps according to another embodiment of the present invention;

FIG. 2-5 is a cross-sectional view illustrating a forehead support with symmetrical straps according to another embodiment of the present invention;

FIG. 2-6 is a cross-sectional view illustrating a forehead support with symmetrical straps according to another embodiment of the present invention;

FIG. 2-7 is a cross-sectional view illustrating a forehead support with asymmetrical straps according to another embodiment of the present invention;

FIG. 2-8 is a cross-sectional view illustrating a forehead support with asymmetrical straps according to another embodiment of the present invention;

FIG. 2-9 is a cross-sectional view illustrating a forehead support with asymmetrical straps according to another embodiment of the present invention;

FIG. 2-10 is a cross-sectional view of a forehead support showing a tension effect according to an embodiment of the present invention;

FIG. 2-11 is a plan view of a forehead support including slots according to an embodiment of the present invention;

FIG. 2-12 is a side view of a forehead support with a bifurcated strap according to an embodiment of the present invention;

FIG. 2-13A is front perspective view of a forehead support according to another embodiment of the present invention; and FIG. 2-13B is a cross-sectional view of the forehead support shown in FIG. 13A.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen.

1. Conventional Forehead Support

Figure 1:
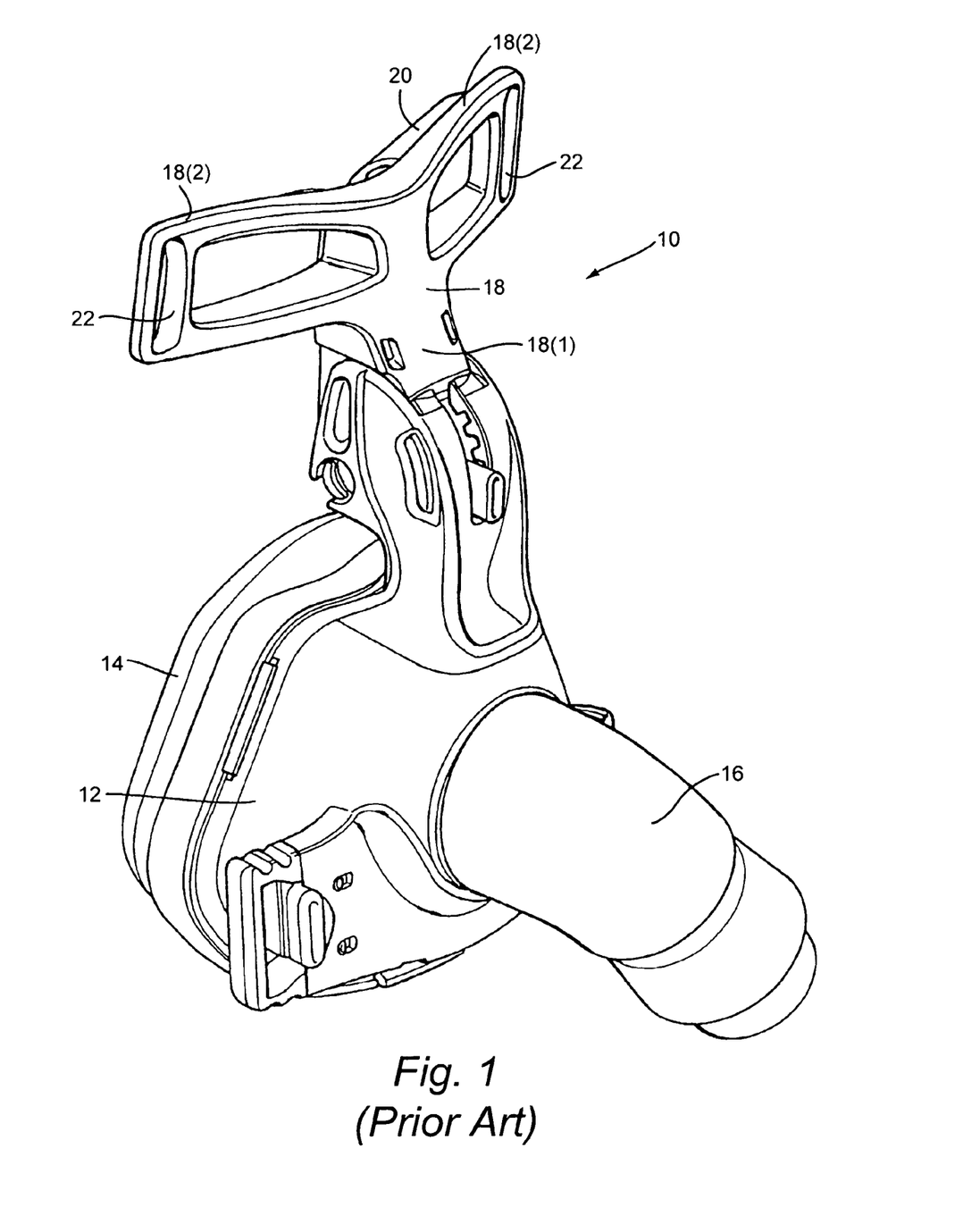
FIG. 1 is a perspective view of a mask including a forehead support as known in the art.

FIG. 1 illustrates a mask 10 as known in the art (e.g., see U.S. Pat. No. 6,532,961). As illustrated, the mask 10 includes a frame 12, a cushion 14 provided to the frame 12 and adapted to form a seal with the patient's face, an elbow 16 provided to the frame 12 and adapted to be connected to an air delivery tube that delivers breathable gas to the patient, and a forehead support 18 to provide a support and stability mechanism between the mask and the patient's forehead. Headgear may be removably attached to the frame 12 and the forehead support 18 to maintain the mask in a desired adjusted position on the patient's face.

The forehead support 18 has a general "T"-shape, with a base 18(1) and a pair of arms 18(2) arranged along the upper cross portion of the "T". Each arm 18(2) includes an elastomeric or foam forehead pad 20 attached thereto, and a slot 22 adapted to engage a respective headgear strap.

2. Forehead Support with Headgear Strap Padding

An aspect of the present invention relates to a forehead support for a mask that is structured such that one or more headgear straps from headgear may be used as forehead padding for the forehead support. That is, the forehead support is not provided with conventional forehead pads (e.g., elastomeric or foam pads), rather one or more headgear straps from headgear are looped through the forehead support in a manner that allows the headgear strap material to function as forehead padding.

As described in greater detail below, the forehead support is structured to support at least a portion of a headgear strap in a manner that positions the strap between the forehead support and the patient's forehead in use. For example, each arm or end portion of the forehead support may provide a headgear strap connector (e.g., crossbar or buckle that defines a slot) that allows the headgear strap to loop around the arm and extend along an inner side facing the patient's forehead. Thus, the forehead support provides a stabilizing or fixing point without the use of a conventional forehead pad.

Each forehead support described below includes a forehead member that acts to reinforce at least a portion of the headgear adjacent the patient's forehead. The forehead member may include a pair of arms adapted to extend laterally along the patient's forehead and may be provided either integrally with the forehead support or as a separate member. The forehead member may be releasably or permanently attached to the headgear.

It should be appreciated that the illustrated forehead member is exemplary and other suitable arrangements are possible. For example, the forehead member may be shorter or longer in length (e.g., arms or wings abbreviated to merely provide structure for strap opening), may include tapered ends to reduce material, and/or may be wider to increase surface area of contact. Many different geometries of the forehead member may be adopted in order to provide a relatively large surface area and hence low contact pressure and to improve lateral stability of the mask in use.

Also, the forehead member may be supported by a base that can be fixedly or adjustably mounted to the mask frame. In an embodiment, the base may be contoured or flexible to help bias the forehead member and hence the headgear straps into the patient's forehead and/or add adjustability to the forehead support in use. In such embodiment, the magnitude of forces to flex the forehead support may be similar to the magnitude of forces to deform the mask seal, which helps to ensure a seal when the forehead support is sufficiently tightened into position.

In an embodiment, the forehead support may merely include an I-beam with an end that provides spaced-apart openings for looping respective headgear straps. In such embodiment, padding (e.g., foam padding) may be provided within the loop defined by the strap to enhance comfort in use.

If the forehead support is rigid, the headgear straps will be a deformable medium that will be pressed against the forehead and become deformed in use. If the forehead support is flexible, the forehead support will deform together with the headgear straps in order to accommodate the forehead shape and distribute the load evenly over the whole contact area.

2.1 Symmetrical Straps

FIG. 2-1 to 2-6 illustrate forehead supports with a forehead member structured to accept left and right forehead straps in a symmetrical manner according to embodiments of the present invention. That is, each side of the forehead member (i.e., both the left-hand side and the right-hand side of the forehead member) is structured such that symmetrical straps loop through the forehead member and the first loop of each strap is through a hole near the vertical plane of symmetry of the mask.

As indicated in the following embodiments, each strap or strap loop may pass through the forehead member or forehead support, one, two, or more times so that the strap is secured in a stable manner.

Also, in the following embodiments, the forehead support can be rigid or flexible, presenting different advantages/disadvantages for each embodiment.

2.1.1 Simple Loop—Velcro®

Figures 1, 21:
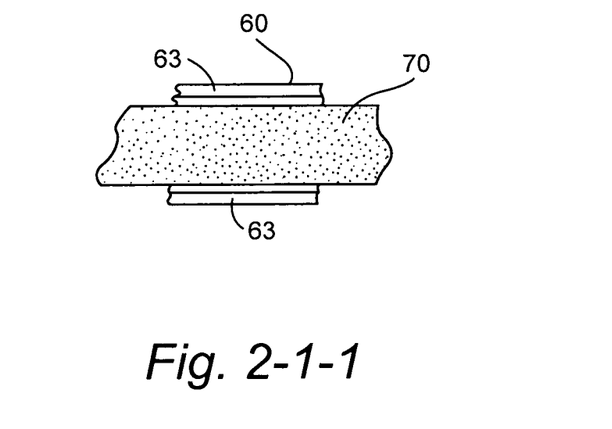
Figures 2, 13A:
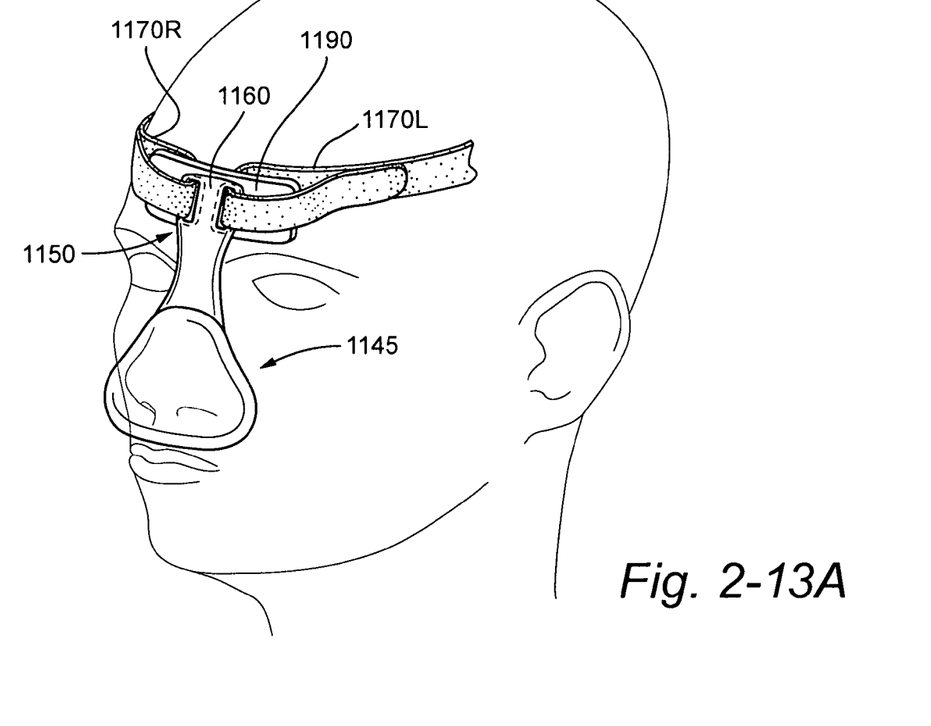
Figures 2, 13B:
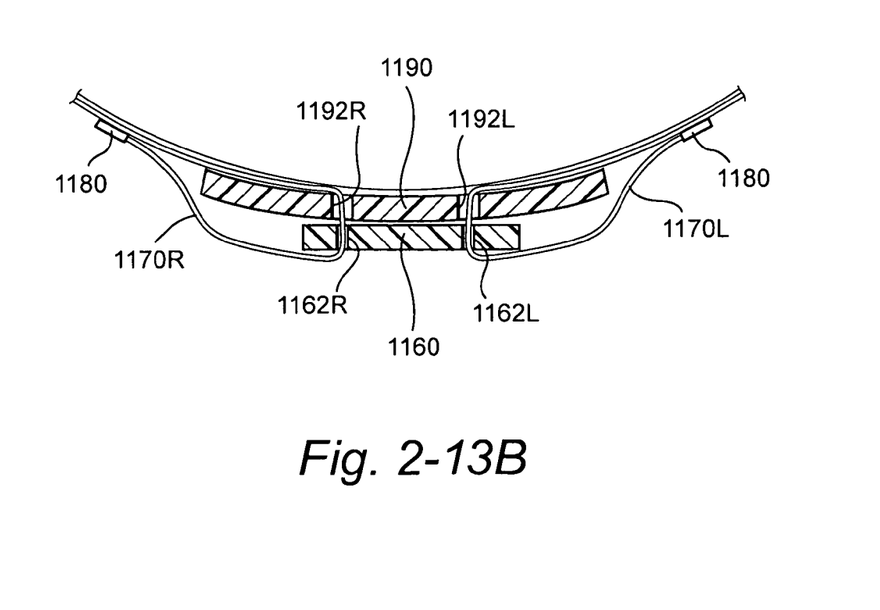
Figure 21:
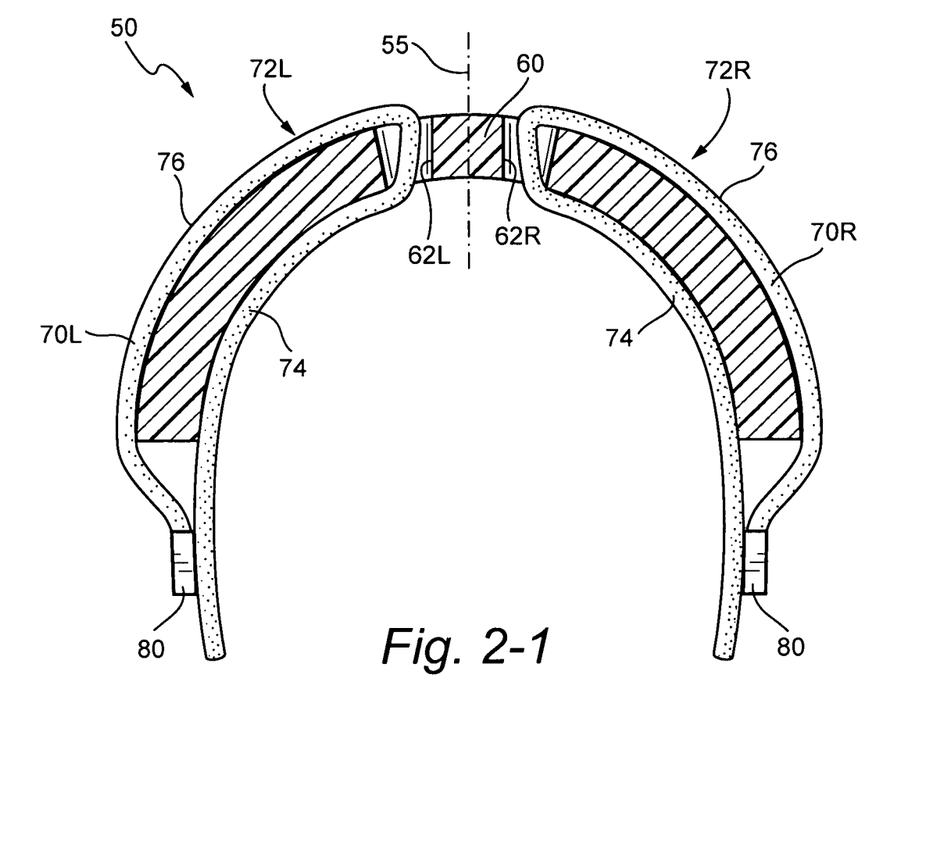

FIG. 2-1 illustrates a forehead support 50 according to an embodiment of the present invention. The forehead support 50 includes a forehead member 60, and each side of the forehead member 60 includes a hole or aperture (i.e., hole 62L on left side and hole 62R on right side of forehead member) near the vertical plane of symmetry 55. As illustrated, left and right headgear straps 70L, 70R are looped through respective holes 62L, 62R near the vertical plane of symmetry so that the left and right headgear straps 70L, 70R cover a large portion of the support area.

That is, each headgear strap 70L, 70R forms a loop 72L, 72R at an end region, with the loops in adjacent opposing relation in use. Each loop 72L, 72R may be secured or closed by a Velcro® attachment 80, which allows for length adjustment. However, each loop may be closed in other suitable arrangements, e.g., sewing, buckle, etc.

As illustrated, each loop 72L, 72R includes an inner side 74 adjacent an inside surface of the forehead member (facing towards the patient's face) and an outer side 76 adjacent an outer surface of the forehead member (facing away from the patient's face). The inner side 74 of the loop along the inside surface provides a layer of headgear between the patient's forehead and the forehead support, which serves as padding to increase patient comfort in use. Specifically, under headgear tension, the headgear padding distributes the load over a large portion of the forehead to avoid forming high pressure contact regions, provides a soft and/or warm to touch contact surface, and interposes a soft, deformable medium between the forehead support and the patient's forehead to ensure that the largest possible portion of the forehead is contacted by the forehead support, reducing the average pressure.

Figure 211:
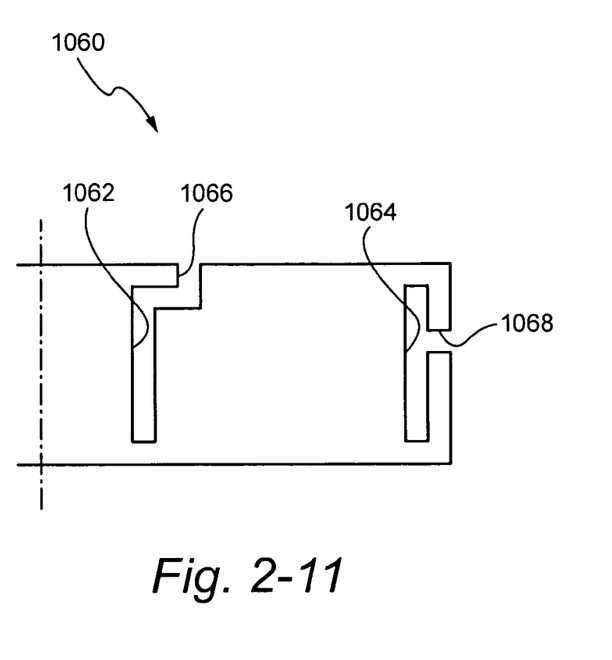
Figure 212:
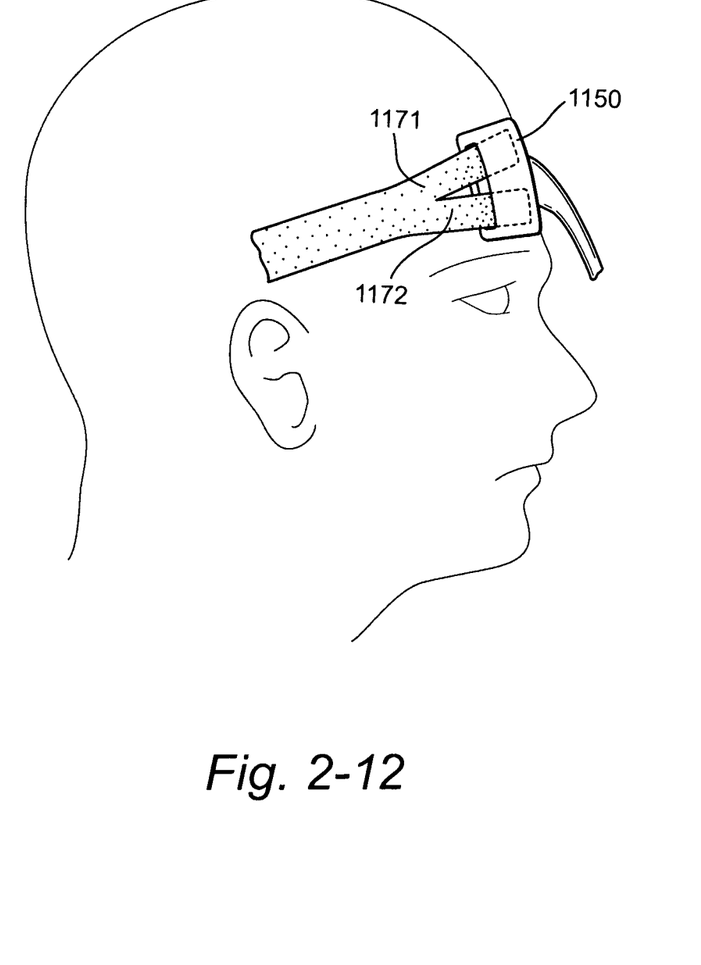

In an embodiment, one or more locating ribs or rims may be provided along a length of the forehead member of the forehead support to prevent relative misalignment between the headgear straps and the forehead support, e.g., prevent relative movements between the straps and the forehead support along a direction normal to the plane of the sheet (i.e., direction is in the superior-inferior plane (i.e., misalignment is due to the headgear strap moving upwards or downwards of the forehead support, thereby exposing the underlying rigid supporting member)) which may cause relative misalignment and may cause the forehead support to contact the patient's forehead. For example, as shown in FIG. 2-1-1, upper and lower edges of the forehead member 60 may provide locating rims 63 along their length that create a channel to receive the headgear strap 70 and guide sliding movement of the strap.

2.1.2 Double Loop from Inside—Velcro®

Figure 22:
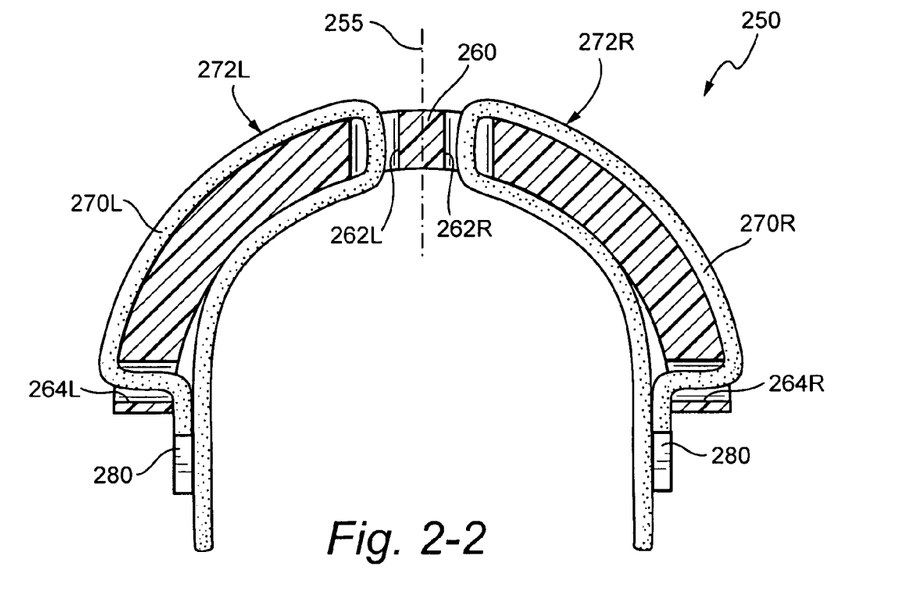

FIG. 2-2 illustrates a forehead support 250 according to another embodiment of the present invention. In this embodiment, each side of the forehead member 260 includes a first, inner hole 262L, 262R near the vertical plane of symmetry 255 and a second, outer hole 264L, 264R near the respective end of the member. As illustrated, each of the left and right headgear straps 270L, 270R is looped through the respective inner hole 262L, 262R near the vertical plane of symmetry so that the strap itself covers a large portion of the support area. Also, each strap 270L, 270R loops back on itself through the outer hole 264L, 264R so that any misalignment between the strap and the forehead support is prevented. Each loop 272L, 272R formed by the strap may be secured by a Velcro® attachment 280. As illustrated, each strap 270L, 270R is looped back on itself towards an inner side of the forehead support, which positions the Velcro® attachment 280 along an inner side.

2.1.3 Double Loop from Outside—Velcro®

Figure 23:
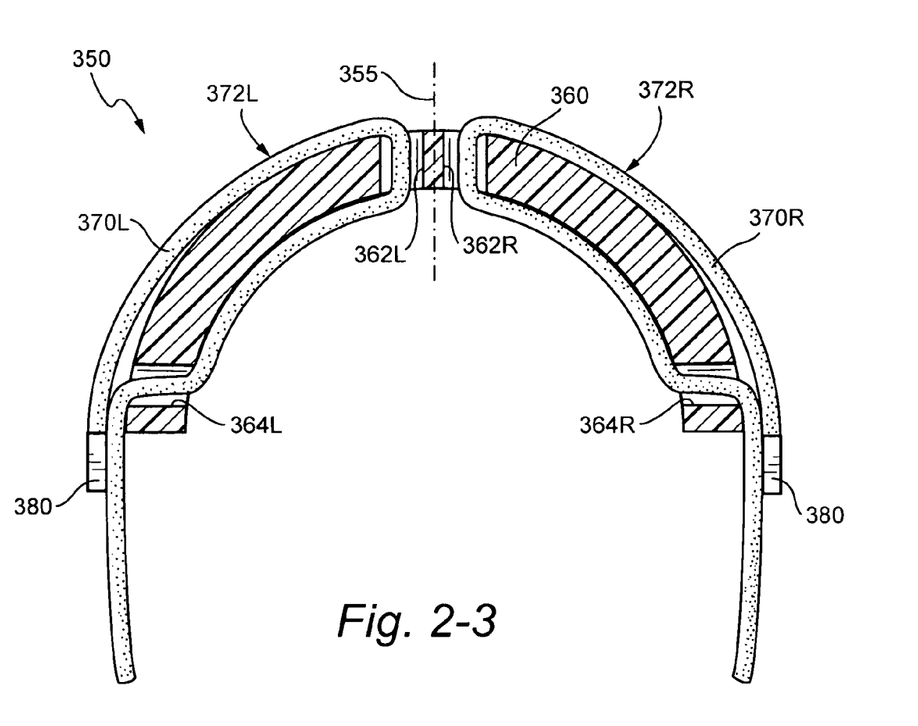

FIG. 2-3 illustrates a forehead support 350 according to another embodiment of the present invention. In this embodiment, each side of the forehead member 360 includes a first, inner hole 362L, 362R near the vertical plane of symmetry 355 and a second, outer hole 364L, 364R near the respective end of the member. As illustrated, each headgear strap 370L, 370R is looped back on itself through the respective second hole 362L, 362R. Each loop 372L, 372R formed by the strap may be secured by a Velcro® attachment 380. As illustrated, each strap 370L, 370R is looped back on itself towards an outer side of the forehead support, which positions the Velcro® attachment 380 along the outer side.

2.1.4 Double Loop from Inside—Buckle

Figure 24:
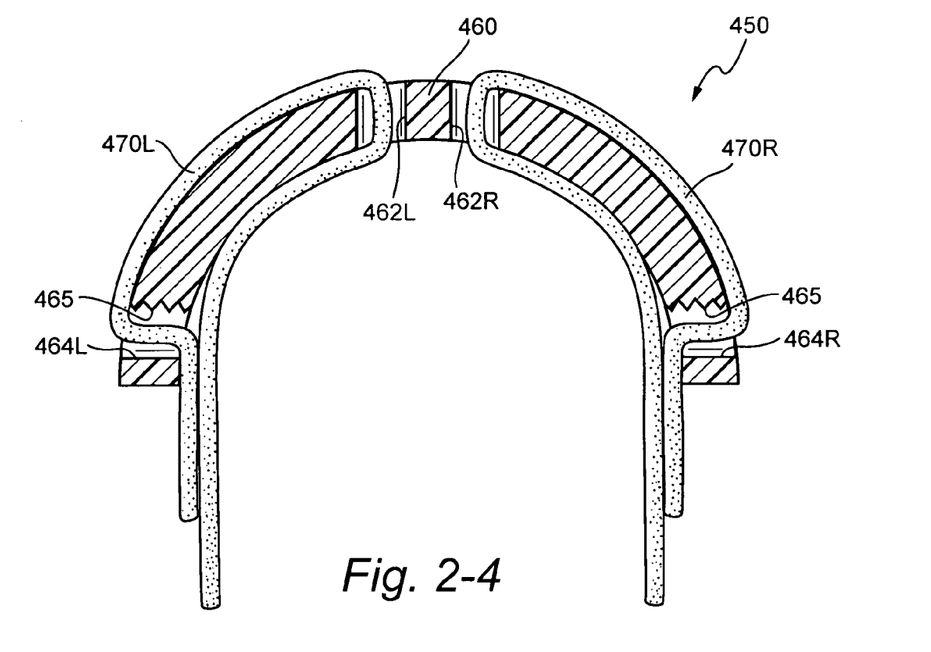

FIG. 2-4 illustrates a forehead support 450 according to another embodiment of the present invention. This embodiment is similar to FIG. 2-2 with the straps 470L, 470R looped through respective first holes 462L, 462R and second holes 464L, 464R of the forehead member 460, and the straps looped back on itself towards an inner side of the forehead support. In contrast, each strap 470L, 470R is secured by using the forehead support as a buckle, which simplifies the headgear manufacturing process and makes it cheaper. For example, each second hole 464L, 464R may include one or more teeth 465 structured to secure the respective strap in position (e.g., ladder lock configuration in headgear buckles).

2.1.5 Simple Buckle with Double Padding

Figure 25:
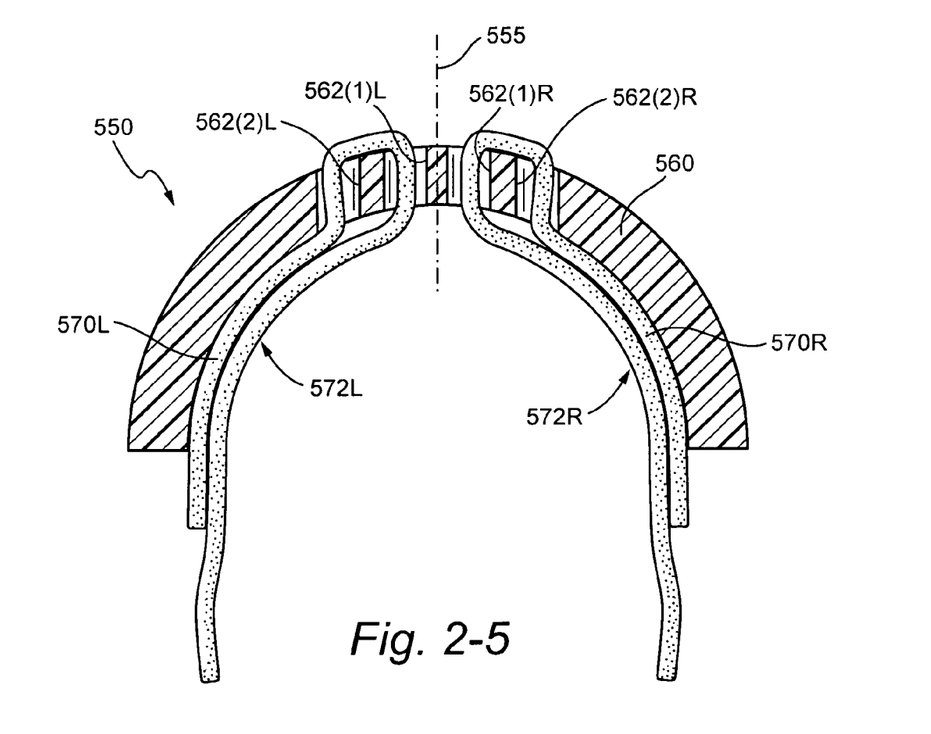

FIG. 2-5 illustrates a forehead support 550 according to another embodiment of the present invention. In this embodiment, each side of the forehead member 560 includes a pair of holes 562(1)L, 562(2)L, 562(1)R, 562(2)R near the vertical plane of symmetry 555. As illustrated, each headgear strap 570L, 570R is looped through the respective pair of holes 562(1)L, 562(2)L, 562(1)R, 562(2)R and back on itself so that both sides of the loop 572L, 572R extend along the inside surface of the forehead member (facing towards the patient's face). This arrangement provides a double layer of headgear interposed between the patient's forehead and the forehead support, which increases the padding effect in use.

Similar to FIG. 2-4, each strap 570L, 570R may be secured by using the forehead support 560 as a buckle. As noted above with respect to FIG. 2-1, one or more locating rims may be provided along a length of the forehead member of the forehead support to improve stability and prevent relative misalignment between the headgear straps and the forehead support.

2.1.6 Multiple Loops with Double Padding

Figure 26:
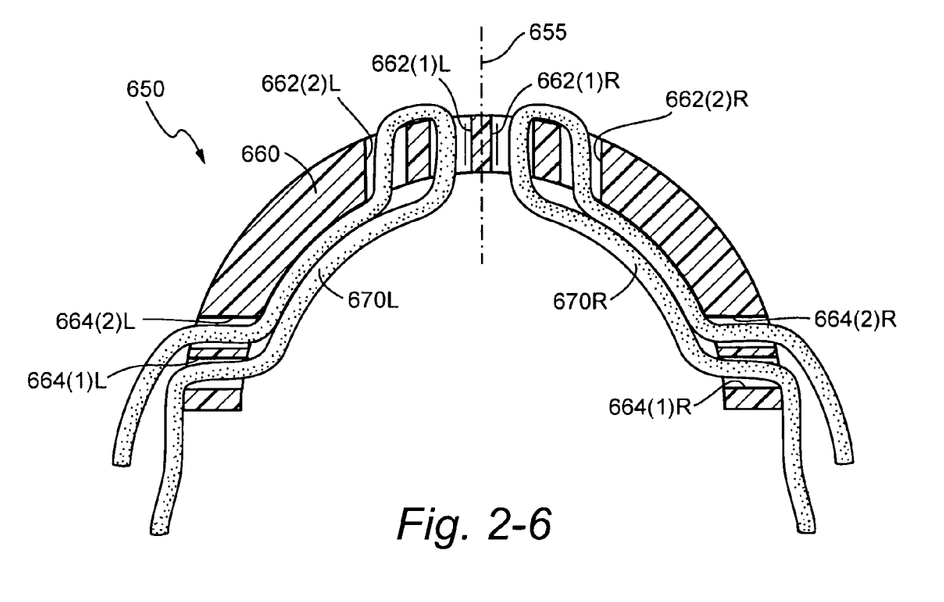

FIG. 2-6 illustrates a forehead support 650 according to another embodiment of the present invention. In this embodiment, each side of the forehead member 660 includes a pair of inner holes 662(1)L, 662(2)L, 662(1)R, 662(2)R near the vertical plane of symmetry 655 and a pair of outer holes 664(1)L, 664(2)L, 664(1)R, 664(2)R near the respective end of the member. As illustrated, each headgear strap 670L, 670R is passed through a respective one of the outer holes 664(1)L, 664(1)R (from outside to inside), looped through respective inner holes 662(1)L, 662(2)L, 662(1)R, 662(2)R, and then passed through the other of the outer holes 664(2)L, 664(2)R (from inside to outside) back on itself towards an outer side of the forehead support.

The strap is looped multiple times in a way that provides a double layer of headgear interposed between the patient's forehead and the forehead support, which increases the padding effect in use. In addition, the forehead support maintains the strap in a manner that improves stability and prevents relative misalignment between the headgear straps and the forehead support.

Each loop may be secured with a Velcro® attachment or with a buckle arrangement as per FIGS. 2-4 and 2-5.

2.2 Asymmetrical Straps

Figure 27:
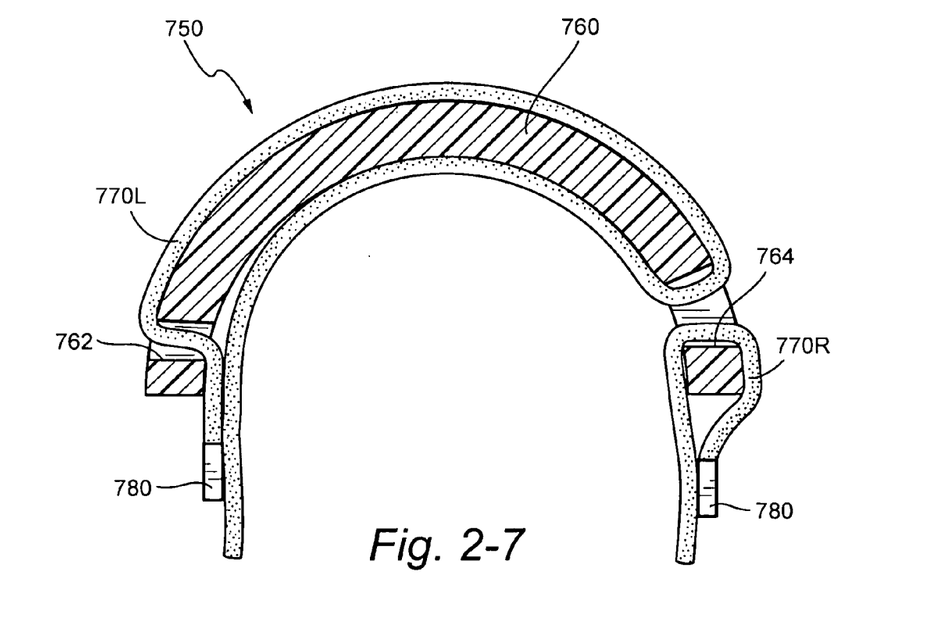
Figure 28:
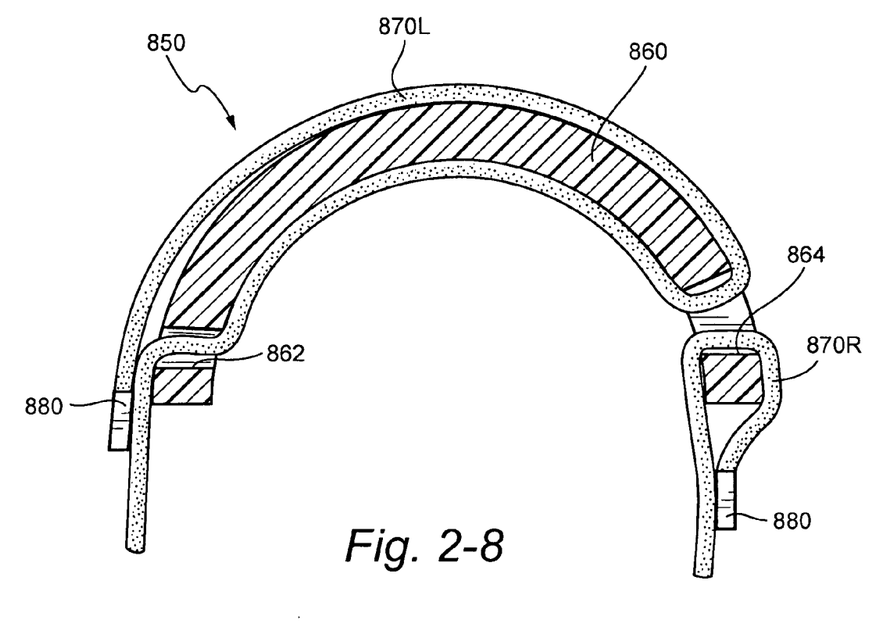
Figure 29:
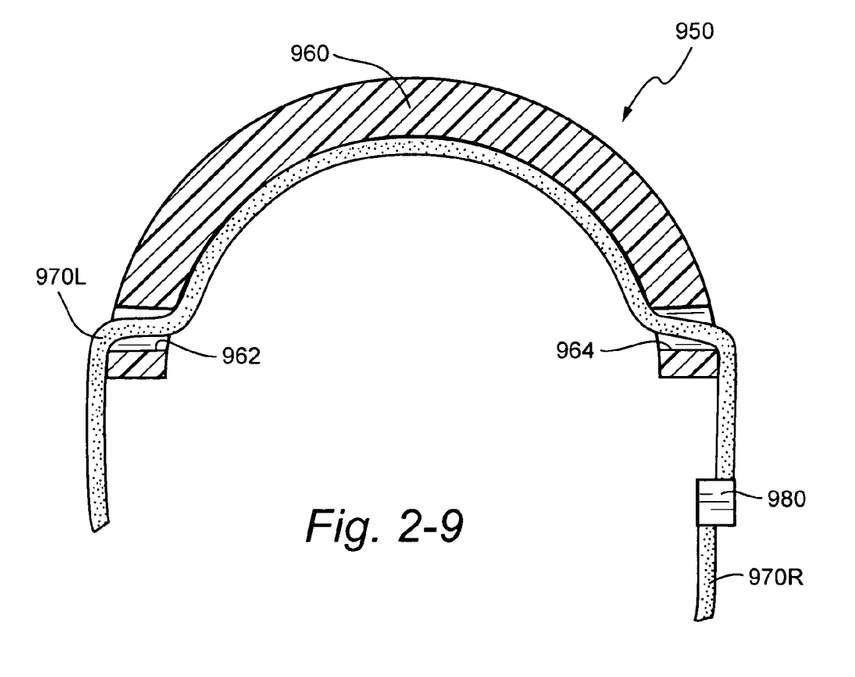

FIGS. 2-7 to 2-9 illustrate embodiments of forehead supports in which headgear straps loop in holes that are not symmetrical with respect to the vertical plane of symmetry.

In the following embodiments, the forehead support can be rigid or flexible, presenting different advantages/disadvantages for each embodiment.

2.2.1 Double Loop from Inside

FIG. 2-7 illustrates a forehead support 750 according to an embodiment of the present invention. The forehead support 750 includes a forehead member 760 including a first, smaller hole 762 adjacent one end of the member (e.g., left side as viewed in FIG. 2-7) and a second, larger hole 764 adjacent the other end of the member (e.g., right side as viewed in FIG. 2-7).

As illustrated, a longer, left headgear strap 770L is looped through the first and second holes 762, 764, and looped back on itself towards an inner side of the forehead support. The longer, left headgear strap 770L may be secured with a Velcro® attachment 780 or with a buckle arrangement. The shorter, right headgear strap 770R is looped through the second hole 764 and may be secured with a Velcro® attachment 780 or with a buckle arrangement. The longer, left headgear strap 770L provides a layer of headgear interposed between the patient's forehead and the forehead support.

2.2.2 Double Loop from Outside

FIG. 2-8 illustrates a forehead support 850 according to another embodiment of the present invention. This embodiment is similar to FIG. 2-7 with first and second holes 862, 864 adjacent respective ends of the forehead member 860. In contrast, the longer, left forehead strap 870L is looped back on itself towards an outer side of the forehead support. The left headgear strap 870L may be secured with a Velcro® attachment 880 or with a buckle arrangement. The shorter, right headgear strap 870R is looped through the second hole 864 and may be secured with a Velcro® attachment 880 or with a buckle arrangement.

2.2.3 Loop with an Additional Buckle

FIG. 2-9 illustrates a forehead support 950 according to another embodiment of the present invention. The forehead support 950 includes a forehead member 960 including a first hole 962 adjacent one end of the member and a second hole 964 adjacent the other end of the member. As illustrated, a longer, left headgear strap 970L loops through the first hole 962 (from outside to inside), passes along the inside surface of the forehead support, and loops through the second hole 964 (from inside to outside) with the free end of the strap extending from the outside of the forehead support.

Thus, the longer, left headgear strap 970L loops all around the patient's forehead and the forehead support and connects to the shorter, right headgear strap 970R, e.g., through a buckle 980 or Velcro® attachment. The left forehead strap 970L may be free to slide inside the first and second support holes 962, 964, e.g., to create a tension effect.

2.3 Tension Effect

The tension of the straps of the headgear can create a spring effect that is additional to the compression of the strap itself when pressed between the patient's forehead and the forehead support. This may be advantageous in biasing the forehead support onto the forehead of the patient, thereby enhancing the seal of the mask. Additionally, the spring effect may eliminate the need for an adjustment mechanism (e.g., a buckle) as the headgear strap will conform to the size of the patient's head.

Figure 210:
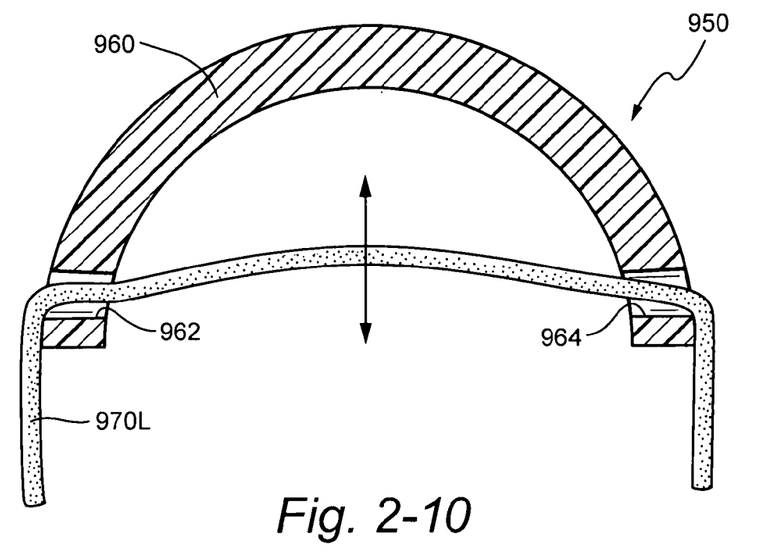

The spring effect is more evident in asymmetrical configurations but is valid for symmetrical ones as well, i.e., the magnitude of the spring effect may depend on the geometry used. For example, FIG. 2-10 illustrates a forehead support 950 similar to that shown in FIG. 2-9 and indicated with similar reference numerals. As illustrated, the headgear strap 970L may be stretched between the holes 962, 964 to place the strap under tension and allow the headgear strap to create a spring effect in use. The tautness of the strap 970L may be adjusted to adjust the spring effect.

2.4 Strap Disengagement

Each hole or slot in the forehead member may include a gap or open side to allow the headgear strap to be fitted without undoing the Velcro® attachment, e.g., and losing the correct headgear length.

For example, FIG. 2-11 illustrates one side of a forehead member 1060 including first and second slots 1062, 1064, with the first slot 1062 including an open side 1066 along its top edge and the second slot 1064 including an open side 1068 along its right edge. As illustrated, the open side 1066 for the first slot 1062 is L-shaped to prevent inadvertent removal of the strap. This arrangement allows straps secured with Velcro® to be disengaged from the forehead support without actually opening the Velcro® itself and thus without losing the headgear setting. This arrangement can be very useful when the headgear needs to be washed and avoids subsequent loss of time setting up the headgear again to achieve good sealing. That is, this arrangement facilitates assembly and disassembly of the headgear straps from the forehead support.

Such quick release arrangement may also be used with straps secured with buckles, e.g., the ResMed Hospital Full-Face Mask quick release buckle configuration could be utilized.

2.5 Other Arrangements

The following provides alternative arrangements of forehead supports.

2.5.1 Forehead Support with Velcro®

As noted above, the top strap of the headgear may be attached to the forehead support with Velcro®. In use, the strap acts as soft padding and the Velcro® stabilizes the strap.

2.5.2 Headgear Clips as Pads

In an embodiment, the top strap of the headgear may be connected to the forehead support via a headgear clip arrangement, i.e., headgear clip associated with a respective headgear strap adapted to be removably interlocked with a clip receptacle provided to the forehead support.

This embodiment functions similarly to the symmetrical strap embodiments (e.g., FIGS. 2-1 to 2-6), but the straps are connected to clips instead of being directly looped around the forehead support. The clips will connect to the forehead support close to the above-mentioned plane of symmetry and will act as proper forehead support. The clips may include padding along an inner surface that is adapted to engage the patient's forehead in use.

2.5.3 Locating Ribs on the Forehead Support

As noted above, one or more locating rims be provided along a length of the forehead member to create a channel in which the straps slide (FIG. 2-1-1). For improved comfort, the rims may be located on the outside surface of the forehead support so that they will not accidentally make contact with the patient's forehead, e.g., due to excessive compression of the straps.

2.5.4 Cut Strap

In an embodiment, each top strap of the headgear may be cut along its longitudinal axis or otherwise produced to provide a pair of spaced-apart straps 1170, 1171, as shown in FIG. 2-12. That is, each top strap may bifurcate into two, spaced-apart straps 1170, 1171 having ends that are looped and secured to the forehead support 1150 in a similar manner as described above. For example, the longer strap in an asymmetrical configuration (e.g., FIGS. 2-7 to 2-9) may be cut along its longitudinal axis so that the longer strap can adapt better to the forehead profile of the patient. Advantageously, this provides a more stable abutment of the straps on the patient's forehead.

2.5.5 Forehead Beam

In an embodiment, the forehead support may have minimal dimensions, e.g., just enough for the straps to loop through. In such embodiment, a flexible beam may be strapped together to the forehead support by the headgear straps. In use, the straps will contact the patient's forehead and the beam will distribute the load according to its rigidity.

For example, FIGS. 2-13A and 2-13B illustrate a mask 1145 including a forehead support 1150 with a forehead member 1160 having a narrow width sufficient for openings 1162L, 1162R. A flexible beam 1190 with openings 1192L, 1192R is aligned with the openings 1162L, 1162R of the forehead member 1160 and coupled therewith via headgear straps 1170L, 1170R. Specifically, each headgear strap 1170L, 1170R is looped through respective openings 1162L, 1162R, 1192L, 1192R of the forehead member 1160 and beam 1190, and the loop may be secured with a Velcro® attachment 1180. The inner side of the loop along the inside surface of the beam 1190 provides a layer of headgear between the patient's forehead and the forehead support, which serves as padding in use.

The beam 1190 is an additional component, which allows its material and rigidity to be chosen separately from the ones of the mask frame and forehead support of the mask. For example, different sizes, materials, and/or rigidity values of the beam may be used to provide a proper load distribution in use.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A respiratory mask, comprising:
  a mask frame;
  a forehead support provided to the mask frame, the forehead support including a forehead member;
  headgear including at least one strap adapted to connect to the forehead member; and
  a flexible component provided to the forehead member and structured to distribute load applied by the at least one strap,
  wherein each of the flexible component and the forehead member includes at least one hole configured and positioned to allow the at least one strap to form a strap loop that loops around at least a portion of the forehead member and arrange at least one layer of the strap loop between at least a portion of the flexible component and the patient's forehead, in use, wherein the flexible component is a separate and distinct component from the forehead member and constructed from a different material than the at least one strap.

2. A respiratory mask according to claim 1, wherein the headgear includes first and second straps, and each side of the forehead member includes said at least one hole configured and positioned to allow the first and second straps to form first and second straps loops that loop around respective portions of the forehead member and arrange the at least one layer of the strap loop between the forehead member and the patient's forehead in use.

3. A respiratory mask according to claim 1, wherein each strap loop is secured by a hook and loop attachment.

4. A respiratory mask according to claim 1, wherein each strap loop is secured by a buckle arrangement.

5. A respiratory mask according to claim 1, wherein the flexible component has a size, material and/or rigidity that is at least partially determinative of load distribution.

6. A respiratory mask according to claim 1, wherein the flexible component extends beyond each lateral edge of the forehead member.

7. A respiratory mask according to claim 6, wherein the flexible component includes two of said at least one holes, each spaced from the edge towards a center of the flexible component.

8. A respiratory mask according to claim 1, wherein the at least one layer of said strap loop forms the only padding layer that contacts the patient's forehead between the forehead member and the patient.

9. A respiratory mask according to claim 1, wherein the at least one layer prevents at least a majority of the flexible component from contacting the patient's forehead in use.

10. A respiratory mask according to claim 1, wherein the flexible component is constructed of a material and/or rigidity that is different than that of the mask frame and/or forehead support.

11. A respiratory mask according to claim 1, wherein the flexible component includes a size, material and/or rigidity that is specifically selected to provide a proper load distribution in use.

12. A respiratory mask according to claim 1, wherein the flexible component includes a specifically chosen rigidity value based on a desired load distribution.

13. A respiratory mask, comprising:
a mask frame;
a forehead support provided to the mask frame, the forehead support including a forehead member; and
headgear including first and second straps extending from lateral sides of the forehead member,
wherein the forehead member includes at least one hole configured and positioned to allow the first and second straps to form first and second strap loops that loop around respective portions of the forehead member, and the first and second strap loops are asymmetrically arranged with respect to a vertical plane of symmetry of the forehead member,
wherein each of the first and second strap loops provides a padding layer between the forehead member and the patient's forehead, and the first and second strap loops are asymmetrically arranged such that the padding layer provided by one of the strap loops covers a larger portion of the forehead member than the padding layer provided by the other of the strap loops.

14. A respiratory mask according to claim 13, wherein each strap loop is secured by a hook and loop attachment.

15. A respiratory mask according to claim 13, wherein each strap loop is secured by a buckle arrangement.

16. A respiratory mask according to claim 13, wherein the forehead support is structured to deform together with the first and second straps.

17. A respiratory mask, comprising:
a mask frame;
a forehead support provided to the mask frame, the forehead support including a forehead member with a first width;
a flexible beam including a second width that is wider than the first width; and
headgear including first and second straps,
wherein the forehead member and the flexible beam each include openings configured and positioned to allow the first and second straps to form first and second strap loops that loop around respective portions of the forehead member and the flexible beam, and a layer of each strap loop is arranged between the flexible beam and the patient's forehead to prevent at least a majority of the flexible beam from contacting the patient's forehead in use whereby the flexible beam is structured to distribute load applied by the layer of each strap loop,
wherein the layers provided by the strap loops arranged between the flexible beam and the patient's forehead cooperate to cover a majority of the flexible beam to prevent said contact of the flexible beam and the patient's forehead in use, and
wherein the flexible beam is a separate and distinct component from the forehead member.

18. A respiratory mask according to claim 17, wherein each strap loop is secured by a hook and loop attachment.

19. A respiratory mask according to claim 17, wherein the flexible beam is constructed of a material and/or rigidity that is different than that of the mask frame and/or forehead support.

20. A respiratory mask according to claim 17, wherein the flexible beam is constructed of a material and/or rigidity that is different than that of the first and second straps.

21. A respiratory mask according to claim 17, wherein the flexible beam has a size, material and/or rigidity that is at least partially determinative of load distribution.

22. A respiratory mask, comprising:
a mask frame;
a forehead support provided to the mask frame, the forehead support comprising a forehead member; and
headgear comprising at least one strap adapted to connect to the forehead member,
wherein the forehead member comprises one or more openings configured and positioned to allow at least one strap to form a strap loop that loops around at least a portion of the forehead member such that at least a portion of the strap loop has one or more layers between the forehead member and the patient's forehead in use, and a flexible component provided to the forehead member, the flexible component constructed of a different material than the at least one strap to at least partly determine the load distribution applied by the strap in use, the one or more layers being arranged between the flexible component and the patient's forehead so as to provide padding between the flexible component and the patient's forehead, thus preventing at least a majority of the flexible component from contacting the patient's forehead in use, and
wherein the flexible component is a separate and distinct component from the forehead member.

23. A respiratory mask according to claim 22, wherein the headgear comprises first and second straps, and each side of the forehead member comprises one or more openings configured and positioned to allow the first and second straps to form first and second strap loops that loop around respective portions of the forehead member and arrange one or more layers of the strap loop between the forehead member and the patient's forehead in use.

24. A respiratory mask according to claim 22, wherein each strap loop is secured by a hook and loop attachment.

25. A respiratory mask according to claim 22, wherein each strap loop is secured by a buckle arrangement.

26. A respiratory mask according to claim 22, wherein the flexible component is constructed of a material and/or rigidity that is different than that of the mask frame and/or forehead support.

27. A respiratory mask according to claim 22, wherein the flexible component is positioned forward of the forehead member closer to the patient's forehead in use.

28. A respiratory mask according to claim 22, wherein the forehead member includes a first width and the flexible component includes a second width that is wider than the first width.

29. A respiratory mask according to claim 22, wherein the forehead member and the flexible component each comprise openings configured and positioned to allow first and second headgear straps to form first and second strap loops that loop around respective portions of the forehead member and the flexible component, and a layer of each strap loop is arranged between the flexible component and the patient's forehead to prevent contact of the flexible component and the patient's forehead in use.

30. A respiratory mask according to claim 22, wherein the forehead member is adapted to extend laterally along the patient's forehead.

31. A respiratory mask according to claim 22, wherein the respiratory mask is a full-face mask or nasal mask.

32. A respiratory mask according to claim 22, further comprising a cushion provided to the mask frame and adapted to form a seal with the patient's face.

33. A respiratory mask according to claim 22, further comprising an elbow provided to the mask frame and adapted to be connected to an air delivery tube.

34. A respiratory mask according to claim 22, wherein the forehead support has a general T-shape.

35. A respiratory mask according to claim 22, wherein the forehead support is a fixedly or adjustably mounted to the mask frame.

36. A respiratory mask, comprising:
a mask frame;
a forehead support provided to the mask frame, the forehead support including a forehead member;
headgear including at least one strap adapted to connect to the forehead member; and
a flexible component provided to the forehead member and structured to distribute load applied by the at least one strap over an area larger than a forehead facing area of the forehead member, in use,
wherein each of the flexible component and the forehead member includes at least one hole configured and positioned to allow the at least one strap to form a strap loop that loops around at least a portion of the forehead member and arrange at least one layer of the strap loop between at least a portion of the flexible component and the patient's forehead, in use and
wherein the flexible component is a separate and distinct component from the forehead member and constructed from a different material than the at least one strap.

37. A respiratory mask according to claim 36, wherein the flexible component is constructed of a material and/or rigidity that is different than that of the mask frame and/or forehead support.

38. A respiratory mask according to claim 36, wherein the at least one layer prevents at least a majority of the flexible component from contacting the patient's forehead in use.

39. A respiratory mask according to claim 36, wherein the flexible component extends beyond each lateral edge of the forehead member.

40. A respiratory mask according to claim 36, wherein the flexible component is deformable to accommodate the shape of the patient's forehead and distribute the load evenly over the whole contact area of the flexible component including contact area adapted to extend along a region of the patient's forehead located above the patient's nasal bridge region.

41. A respiratory mask, comprising:
a mask frame;
a forehead support provided to the mask frame;
headgear including at least one strap adapted to connect to the forehead support; and
a flexible component provided to the forehead support and structured to distribute load applied by the at least one strap,
wherein the flexible component and the forehead support are configured and positioned to allow the at least one strap to form a strap loop that loops around at least a portion of the flexible component and arrange at least one layer of the strap loop between at least a portion of the flexible component and the patient's forehead, in use,
wherein the flexible component is deformable to accommodate the shape of the patient's forehead and distribute the load evenly over the whole contact area of the flexible component including contact area adapted to extend along a region of the patient's forehead located above the patient's nasal bridge region,
wherein the flexible component is constructed from a different material than the at least one strap; and
wherein the at least one layer prevents at least a majority of the flexible component from contacting the patient's forehead in use.

42. A respiratory mask according to claim 41, wherein the forehead support includes a forehead member and the flexible component is provided to the forehead member as a separate and distinct component from the forehead member.

43. A respiratory mask according to claim 42, wherein each of the flexible component and the forehead member includes at least one hole configured and positioned to allow the at least one strap to form the strap loop.

44. A respiratory mask according to claim 41, wherein the flexible component is constructed of a material and/or rigidity that is different than that of the mask frame and/or forehead support.

45. A respiratory mask, comprising:
a mask frame;
a forehead support provided to the mask frame;
headgear including at least one strap adapted to connect to the forehead support;
and a flexible component provided to the forehead support and structured to distribute load applied by the at least one strap,
wherein the flexible component and the forehead support are configured and positioned to allow the at least one strap to form a strap loop that loops around at least a portion of the flexible component and arrange at least one layer of the strap loop between at least a portion of the flexible component and the patient's forehead, in use, wherein the flexible component is deformable to accommodate the shape of the patient's forehead and distribute the load evenly over the whole contact area of the flexible component including contact area adapted to extend along a region of the patient's forehead located above the patient's nasal bridge region;

wherein the flexible component is constructed from a different material from the at least one strap;

wherein the forehead support includes a forehead member and the flexible component is provided to the forehead member as a separate and distinct component from the forehead member; and wherein each of the flexible component and the forehead member includes at least one hole configured and positioned to allow the at least one strap to form the strap loop.

* * * * *